United States Patent [19]

Dean

[11] Patent Number: 4,673,524

[45] Date of Patent: Jun. 16, 1987

[54] CLEANER COMPOSITION

[76] Inventor: Ralph R. Dean, P.O. Box 1492, Fort Worth, Tex. 76101

[21] Appl. No.: 863,847

[22] Filed: May 16, 1986

[51] Int. Cl.$^4$ .......................... C11D 9/30; C11D 17/00
[52] U.S. Cl. ..................................... 252/118; 252/117; 252/122; 252/153; 252/170; 252/171; 252/174.22; 252/DIG. 14
[58] Field of Search .................. 252/118, 122, 174.22, 252/89.1, 170, 117, 153, 171, DIG. 14

[56] References Cited

U.S. PATENT DOCUMENTS

| | | | |
|---|---|---|---|
| 3,882,038 | 5/1975 | Clayton et al. | 252/170 |
| 4,075,234 | 2/1978 | Peterson | 562/590 |
| 4,129,520 | 12/1978 | Peterson | 252/122 |
| 4,252,663 | 2/1981 | Eriksson | 252/99 |
| 4,617,251 | 10/1986 | Sizensky | 252/170 |

Primary Examiner—Josephine L. Barr
Attorney, Agent, or Firm—James C. Fails; William T. Wofford; Arthur F. Zobal

[57] ABSTRACT

A cleaner for cleaning from hands and the like difficultly removable objectionable material such as modern catalyzed auto paint, fast drying printers ink and the like characterized by a multi-component composition that includes at twenty-five percent by weight and no more than sixty percent by weight of dibasic ester consisting essentially of an admixture of dimethyl succinate, dimethyl glutarate and dimethyl adipate; at least five percent by weight and no more than twenty-five percent by weight of dipropylene glycol methyl ether; at least five percent by weight and no more than twenty-five percent by weight of oderless mineral spirits; at least four percent and no more than nine percent by weight of triethanolamine; at leat five percent and no more than fifteen percent by weight of octylphenoxypolyethoxyethanol in which there are seven to eight moles ethylene oxide per mole of octyl phenol; at least one percent and no more than three percent by weight of nonyl phenol ethoxylate having about four moles of ethylene oxide per mole of nonyl phenol; and at least eight and no more than eighteen percent by weight of tall oil fatty acid.

2 Claims, No Drawings

CLEANER COMPOSITION

FIELD OF THE INVENTION

This invention relates to new classes of compositions designed for dissolving and removing difficultly removable material. More particularly, this invention relates to compositions that, in fact, employ no water and can be used to remove from the hands or the like even freshly dried, difficultly removable material; such as, modern catalyzed industrial coatings, fast drying printers' ink and the like; as well as for special purpose applications.

DESCRIPTION OF THE PRIOR ART

The compositions can be understood more nearly completely by examining their respective uses, such as hand cleaning, throat pump lubricants, other cleaning and the like.

The prior art has seen the development of a wide variety of hand cleaners for cleaning various substances from hands, including the so-called waterless compositions, even though these "waterless" compositions employ up to forty percent (40%) by weight of water.

None of the prior art compositions could be employed successfully for removing difficultly removable objectionable material like modern catalyzed automobile paints, other industrial coatings, fast drying printers' ink and the like. Some of the unsuccessful approaches tried in the prior art involved the use of hydrophilic surfactants that liked water, hydrophobic surfactant compositions that did not like water and were not miscible with water and compositions that had both hydrophilic and hydrophobic properties so that they were miscible to a lesser extent in both oil and water compositions. The latter proved to be the more nearly successful of the prior art compositions and worked well with conventional greases, oils and dirt that the automobile mechanic ordinarily encounters. They did not work well, however, with the modern catalyzed automobile paints which the paint technicians got on their hands, with fast drying printers' ink which the printing technicians got on their hands, or other similarly difficultly removable objectionable material; particularly when the difficultly removable objectionable materials where freshly dried.

Typical liquid hand cleaners have employed monoethanolamine, oleic acid, dichlorobenzene, dipropylmethylglycol ether, glycerine and water. Typical waterless hand cleaners of the prior art have employed kerosene, stearic acid, Igepal CO-530 surfactant, water, dipropylene glycol, and dipropylene glycol monomethyl ether.

Kirk-Othmer *ENCYCLOPEDIA OF CHEMICAL TECHNOLOGY*, "Chem Abstracts", and "Journal of Paint Technology", and other such references have a good discussion of solubility theory. Once individual components are examined, there are a wide variety of technical bulletins and publications by suppliers of these individual components. For example, duPont has a good discussion in its notes on its technical bulletin on dibasic esters, referring to a variety of literature and patent references on dimethyl glutarate.

Since none of the prior art gave a workable hand cleaner, it has been commercial practice for people in the art, such as paint technicians, printer technicians and the like to use unapproved chemicals to remove the paint or the printers' ink from their hands. For example, material such as phenol, acetone, methyl ethyl ketone, toluol, and even agents such as butyl Cellosolve, that are reputedly carcinogenic materials have been employed in practice for cleaning hands, even though not approved by OSHA (Office of Safety and Health Administration). These unsafe materials caused cracked skin, and other immediate undesirable effects, not to mention more serious and unknown longer term effects that are adverse to the health of the technician, or worker. Thus it can be seen that there is a crying need for a hand cleaner that can be safely employed for cleaning the difficultly removable objectionable materials from hands without imperiling the health of the worker.

One of the illustrative special purpose applications is referred to as "throat seal lubricant". A purpose of the "throat seal lubricant", for example, is to keep a piston rod in a pump or air compressor constantly lubricated and to dissolve undesirable deposits such as paint specks, carbonaceous deposits and the like.

SUMMARY OF THE INVENTION

Accordingly, it is an object of this invention to provide a hand cleaner that can be successfully employed for removing difficultly removable objectionable material from the hands or the like of a workman without imperiling the health of the worker.

It is a specific object of this invention to provide a safe hand cleaner than can be employed to remove difficultly removable objectionable materials such as automobile paint, fast drying printers' ink and the like from portions of the anatomy of the worker without adversely affecting the health of a worker over a long term of use.

These and other objects will be more nearly completely understood from the descriptive matter hereinafter.

In accordance with this invention there is provided a hand cleaner for cleaning from hands and the like difficultly removable objectionable material such as modern automobile paint, fast drying printers' ink and the like characterized by:

a. at least twenty-five percent (25%) by weight and no more than sixty percent (60%) by weight of dibasic ester consisting essentially of an admixture of dimethyl succinate, dimethyl glutarate and dimethyl adipate;

b. at least five percent (5%) by weight and no more than twenty-five percent (25%) by weight of dipropylene glycol methyl ether;

c. at least five percent (5%) by weight and no more than twenty-five percent (25%) by weight of odorless mineral spirits;

d. at least four percent (4%) and no more than nine percent (9%) by weight of triethanolamine;

e. at least five percent (5%) and no more than fifteen percent (15%) by weight of octylphenoxypolyethoxyethanol in which there are seven to eight moles ethylene oxide per mole of octyl phenol;

f. at least one percent (1%) and no more than three percent (3%) by weight of nonyl phenol ethoxylate having about four moles of ethylene oxide per mole of nonyl phenol; and g. at least eight percent (8%) and no more than eighteen percent (18%) by weight of tall oil fatty acid.

Preferably the hand cleaner has a concentration in percent by weight of about 38.5 percent dibasic ester, fifteen percent (15%) dipropylene glycol methyl ether, fifteen percent (15%) odorless mineral spirits, 6.5 percent triethanolamine, ten percent (10%) by weight of octylphenoxypolyethoxyethanol, two percent (2%) by weight of nonyl phenol ethoxylate and thirteen percent (13%) by weight of tall oil fatty acid.

DESCRIPTION OF PREFERRED EMBODIMENT

There are many types of objectionable materials; including the new catalyzed industrial coatings, fast drying printers' inks that also include highly volatile components with difficultly removable residues suspended therewithin; that present a problem with cleaning items such as hands, pump seals and the like. In fact, the prior art practical workplace has seen the use of materials that cause damage to skin or otherwise adversely affect the health of the worker or user. Accordingly, it is particularly desired to provide a hand cleaner that incorporates only approved and safe constituents, yet still is effective for removing difficultly removable objectionable materials, even freshly dried, without adversely affecting the health of the user over a long period of use.

Because of the urgency of this need to provide a safe hand cleaner that is still effective, there has not been time for the performance of exhaustive research, although many formulations have been tried to arrive at a workable hand cleaner employing approved constituents, or ingredients. This hand cleaner formulation, or composition, is result of such a concentrated research effort testing many different formulations to try to resolve this long standing and urgent need.

As set forth regarding the composition hereinbefore, the particular components are recognized safe and have been priorly approved from a standpoint of their toxicity to humans, although in other context.

It should be noted that the compositions of this invention may be widely useful in addition to cleaning hands or as pump seal lubricants. For example, the compositions can be employed for cleaning the difficultly removable materials from clothing, carpets, and painting equipment (usually by soaking in the compositions), as in prior cleaning approaches in prior compositions.

The dibasic esters are described in commercially available literature, such as from duPont. In that literature there are described multiple classes of dibasic esters. What is employed herein is the basic dibasic ester, referred to as DBE, containing an admixture of dimethyl adipate, dimethyl glutararate, dimethyl succinate. The typical weight percent compositions include sixteen percent (16%) by weight of dimethyl adipate, sixty-one percent (61%) by weight of dimethyl glutarate, and twenty-two point five percent (22.5%) by weight of dimethyl succinate. The remainder of the composition of about zero point five percent (0.5%) by weight may contain impurities that make advisable precautionary measures to prevent a buildup sufficient to cause an accident. For example, up to one part per million of cyanide ion has been reported and up to ten parts per million of methyl alcohol has been reported. This makes advisable preventing of accumulation in sink drains or the like in case acid should be later poured down the sink drain and cause evolution of toxic materials such as hydrogen cyanide. Moreover, the methyl alcohol could conceivably cause blindness or other undesirable health effects if allowed to build up over a protracted interval. These contingencies are so remote, considering the ordinary use of hand cleaners and the way hands are wiped on rags that are subsequently disposed of by burning, that there is no safety hazard. Nevertheless, instructions on the use of the product will contain a warning of this possibility. The material safety data sheet has been supplied by E. I. duPont de Nemours and Company, Inc. and is available upon request from either duPont or the U.S. Department of Labor, Occupational Safety and Health Administration.

The dipropylene glycol methyl ether, similarly, is described in commercially available brochures, as from Dow Chemical Company with its DOWANOL (trademark) series. That brochure describes the inclusion of DOWANOL P-Mix or DOWANOL DPM for preventing production of cloudiness in concentrated liquid soaps over an extended period of time. That brochure also discloses the use of DOWANOL DPM for rust preventative and points out that it is non-toxic. The material safety data sheet has been supplied to OSHA by Dow Chemical and is available on request from either Dow or U.S. Department of Labor, Occupational Safety and Health Administration.

The odorless mineral spirits are petroleum solvents having a boiling point of from 191° to 244° C. that are in the form of a water-white liquid having a mild pleasant hydrocarbon odor. They are commercially available from Exxon as "608 solvent". The material safety data sheet has been supplied to OSHA by Exxon Company and is available upon request from either Exxon or the U.S. Department of Labor.

Triethanolamine, as is recognized, is $\beta,\beta',\beta''$ trihydroxytriethylamine and is defined in HACKH'S CHEMICAL DICTIONARY, fourth edition, Julious Grant editor, McGraw Hill Book Company, New York, N.Y., page 212. It is commercially available from a Union Carbide Corporation, Industrial Chemicals Division, Danbury, Conn., 06817-0001. The material safety data sheet has been submitted to the U.S. Department of Labor and is available upon request from either Union Carbide or OSHA.

The octylphenoxypolyethoxyethanol that is employed herein is commercially available from Rohm and Haas Company, Philadelphia, Pa, 19105 as Triton (registered trademark) X-114 surfactant. It has about 7-8 moles on the average, of ethylene oxide per mole of octyl phenol. As will be appreciated, the 7 to 8 moles of ethylene oxide induce a degree of hydrophilic behavior such that it tends to introduce solubility in water or water base constituents. The material safety data sheet has been supplied to OSHA by Rohm and Haas and is available upon request from either Rohm and Haas or the U.S. Department of Labor.

The nonyl phenol ethoxylate, is an non-ionic surfactant similar to the octylphenoxypolyethoxyethanol but it has an average of only about 4 moles of ethylene oxide per mole of nonyl phenol. This introduces a higher degree of hydrophobic behavior which tends to solubilize elements that are not water soluble, or oil-like substances. It is preferred to use about one part of the nonyl phenol ethoxylate to about five parts of the octylphenoxypolyethoxyethanol in order to achieve the right balance of hydrophobic-hydrophilic behavior in the cleaner in which the non-ionic surfactants are employed. It is commercially available from Union Carbide as Tergitol NP-4 (trademark). The material safety data sheet for nonyl phenol ethoxylate has been submitted by Union Carbide giving the chemical name nonyl phenol polyethylene glycol ether for the non-inert surfactant under the trademark Tergitol NP-4. The material safety data sheet is available upon request from either Union Carbide or OSHA.

The tall oil fatty acid is a by-product from the sulphate wood pulp digestion, mainly resin acids and fatty acids, such as linoleic acid abietic (Steele) acid; linolenic and some oleic acid with 2, 2'-dihydrostigmasterol and lignoceryl alcohol. It is widely used in soaps, varnishes and fruit sprays. It is defined in HACKH'S CHEMICAL DICTIONARY, Fourth Edition, Julious Grant, editor, McGraw Hill Book Company, New York, N.Y., page 660. It is available commercially from Westvaco Corp., Charleston Heights, S.C. 29405. The material safety data sheet has been submitted to the Department of Labor by Westvaco and is available upon request from either Westvaco or OSHA.

The concentrations set forth herein are in percent by weight unless otherwise specified.

As indicated hereinbefore, the dibasic esters are used in the concentrations of at least twenty-five percent (25%) by weight and no more than sixty percent (60%) by weight of the composition for forming the cleaner for cleaning hands or the like. Preferably an amount of about thirty-eight point five percent (38.5%) by weight is employed in the composition to form an optimum admixture that is surprisingly effective.

If less than about twenty-five percent (25%) by weight of dibasic ester is employed, the "hand cleaner" is relatively ineffective and only does a mediocre job of cleaning catalyzed paints from hands. If more than about sixty percent (60%) by weight is employed, it appears to be a waste of the product that is relatively expensive, since it does not improve performance of the composition.

The dipropylene glycol methyl ether is preferably employed in an amount of at least five percent (5%) and no more than about twenty-five (25%) percent by weight of the composition forming the hand cleaner. If less than about five percent (5%) is employed, the penetrating action is too little and there is too little coupling of the remainder of the ingredients with the dibasic ester so the hand cleaner is less effective than desired. If, on the other hand, more than about twentyfive percent (25%) is employed there appears to be a waste of a relatively expensive composition, since it does not improve the composition for cleaning hands. An optimum amount of dipropylene glycol methyl ether is about fifteen percent (15%) by weight to form a composition that is surprisingly effective.

The odorless mineral spirits is employed in a concentration of at least five percent (5%) by weight and no more than twenty-five percent (25%) by weight. Preferably an amount of about fifteen percent (15%) by weight is employed. If less than five percent (5%) by weight of the odorless mineral spirits is employed, there is inadequate cleaning of the hydrophobic constituents of the objectionable material, since there is inadequate hydrophobic solubility. On the other hand, no more than twenty-five percent (25%) by weight should be employed in order to prevent the introduction of fire hazards and inadequate cleaning of the hydrophilic objectionable material.

The triethanolamine is employed in a concentration of at least four percent (4%) by weight and no more than nine percent (9%) by weight. The optimum amount of triethanolamine is about six point six percent (6.6%) by weight in the composition forming the hand cleaner. As is recognized the triethanolamine is one of the family of secondary and tertiary amines and can react with some of the exotic constituents of the modern day paints and fast drying inks and the like.

The octylphenoxypolyethoxyethanol should be employed at least in the amount of five percent (5%) and no more than fifteen percent (15%) by weight; the preferred concentration being about ten percent (10%) by weight; and should be employed with the nonyl phenol ethoxylate in a ratio of about 5:1.

Expressed otherwise the nonyl phenol ethoxylate should be employed in a concentrate of at least one percent (1%) and no more than three percent (3%) by weight in order to form, in combination with the octophenoxypolyethoxyethanol, a non-ionic surfactant having desired hydrophobic-hydrophylic balance of behavior.

The tall oil fatty acid should be employed in a concentration of at least eight percent (8%) and no more than eighteen percent (18%) by weight with an optimum concentration being about thirteen percent (13%) by weight. This allows the biodegradable, soapy behavior to be at a proper level for maximum cleaning.

Toxicological studies have been performed by North Texas University and the Texas College of Osteopathic Medicine. The hand cleaner of this invention forms a cleaner that provides rapid solvency for paints, inks and greases together with cleaning ordinary objectionable materials like soil and the like.

If desired, suitable inert materials can be employed. Typically a preferred type of filler might be Cabosil, a trademark of Cabot Chemical, for blown fines of silica. This forms a mild abrasive that has the desired density not to try to settle out too rapidly. On the other hand, finely divided silica, pumice or the like could be employed, although their density is great enough that they tend to settle. Consequently, when these heavier filler elements are employed, it is preferable to employ a gelling agent to hold the particles in suspension.

In practicing the invention, predetermined quantities of the respective ingredients are introduced into a vat having a paddle mixer or the like. The elements are relatively easily mixed together. The proportions are predetermined to get the desired concentrations of the respective elements. Thereafter, the cleaner is admixed and packaged as desired. For example, it may be packaged in large drums and the like for shipment to large users, such as large paint shops, large print shops or the like. Of course, smaller retail size containers of the cleaner could be prepared if desired.

The following example illustrates the best known example of the specific hand cleaner composition of this invention. It has been particularly effective in cleaning difficultly removable materials such as modern automobile paint from the hands of a worker on whom it was tried.

EXAMPLE

In this example, there was prepared a basic hand cleaning composition by employing thirty-eight point five percent (38.5%) by weight of dibasic ester, fifteen percent (15%) by weight of DPM (Dipropylene Glycol Methyl Ether), about fifteen percent (15%) by weight of odorless mineral spirits in the form of 608 solvent from Exxon, about six point six percent (6.6%) by weight of triethanolamine, commercial grade from Union Carbide, about ten percent (10%) by weight of octophenoxypolyethoxyethanol in the form of Triton X-114, from Rohm and Haas, about two percent (2%) by weight of nonyl phenol ethoxylate in the form of Tergitol NP-4 from Union Carbide and thirteen percent (13%) by weight of tall oil fatty acid from Westvaco Corp.

The quantities were admixed into a unitary formulation in a batch mixture.

The resulting composition was particularly effective removing the automobile paint from the hands.

The composition forming the hand cleaner has a pleasant odor without the addition of any odorizing agents. If desired, however, suitable odorizing agents such as pine scents, lemon scents or the like can be employed. When such scenting compositions are employed, they are usually employed in only trace concentrations, much less than one percent (1%) by weight, for example.

The inventors have been asked to develop this safe hand cleaner because of the unsafe use of aromatic solvents and other potentially hazardous cleaners by employees in large paint shops, print shops and the like. Consequently, this composition is being rushed to market. There may be other equivalent chemicals that could be employed but applicant has not been able to delineate them although many compositions have been tested and have failed to give the same good results.

This invention has enabled providing a safe, effective cleaner for cleaning objectionable materials from hands or the like, in applications where other skin cleaners have not been successful. Thus, it can be seen that this inventon achieves the obvious delineated hereinbefore.

Having thus described the invention, it will be understood that such description has been given by way of illustration and example and not by way of limitation, reference for the latter purpose being had to the appended claims.

What is claimed is:

1. A cleaner for cleaning from items, even freshly dried, difficultly removable objectionable material comprising:
   a. at least twenty-five percent (25%) by weight and no more than sixty percent (60%) by weight of dibasic ester consisting essentially of an admixture of dimethyl succinate, dimethyl glutarate and dimethyl adipate;
   b. at least five percent (5%) by weight and no more than twenty-five percent (25%) by weight of dipropylene glycol methyl ether;
   c. at least five percent (5%) by weight and no more than twenty-five percent (25%) by weight of odorless mineral spirits;
   d. at least four percent (4%) and no more than nine percent (9%) by weight of triethanolamine;
   e. at least five percent (5%) and no more than fifteen percent (15%) by weight of octylphenoxypolyethoxyethanol in which there are seven to eight moles ethylene oxide per mole of octyl phenol;
   f. at least one percent (1%) and no more than three percent (3%) by weight of nonyl phenol ethoxylate having about four moles of ethylene oxide per mole of nonyl phenol; and
   g. at least eight percent (8%) and no more than eighteen percent (18%) by weight of tall oil fatty acid.

2. The cleaner of claim 1 wherein said dibasic ester is present in a concentration of about 38.5 percent by weight; said dipropylene glycol methyl ether is present in a concentration of about fifteen percent (15%) by weight; said odorless mineral spirits is present in about fifteen percent (15%) by weight, said triethanolamine is present in a concentration of about 6.5 percent by weight, said octylphenoxypolyethoxyethanol is present in a concentration of about ten percent (10%) by weight, said nonyl phenol ethoxylate is present in about two percent (2%) by weight and said tall oil fatty acid is present in a concentration of about thirteen percent (13%) by weight.

* * * * *